(12) United States Patent
Nakanishi et al.

(10) Patent No.: US 9,737,279 B2
(45) Date of Patent: Aug. 22, 2017

(54) X-RAY CT APPARATUS

(71) Applicant: Toshiba Medical Systems Corporation, Otawara-shi (JP)

(72) Inventors: Satoru Nakanishi, Arlington Heights, IL (US); Naruomi Akino, Nasushiobara (JP); Yoshinori Uebayashi, Utsunomiya (JP); Takahiro Goto, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 349 days.

(21) Appl. No.: 14/360,771

(22) PCT Filed: Aug. 29, 2013

(86) PCT No.: PCT/JP2013/073192
§ 371 (c)(1),
(2) Date: May 27, 2014

(87) PCT Pub. No.: WO2014/034797
PCT Pub. Date: Mar. 6, 2014

(65) Prior Publication Data
US 2015/0030118 A1   Jan. 29, 2015

(30) Foreign Application Priority Data

Aug. 31, 2012  (JP) ................................. 2012-190844
Aug. 29, 2013  (JP) ................................. 2013-177495

(51) Int. Cl.
*A61B 6/03* (2006.01)
*G06T 11/00* (2006.01)
*A61B 6/00* (2006.01)

(52) U.S. Cl.
CPC .............. *A61B 6/54* (2013.01); *G06T 11/005* (2013.01); *A61B 6/032* (2013.01); *A61B 6/5205* (2013.01);
(Continued)

(58) Field of Classification Search
CPC .... A61B 6/00; A61B 6/02; A61B 6/03; A61B 6/032; A61B 6/52; A61B 6/54;
(Continued)

(56) References Cited

U.S. PATENT DOCUMENTS 7,212,602 B2   5/2007   Tsujii
7,409,033 B2   8/2008   Zhu et al.
(Continued)

FOREIGN PATENT DOCUMENTS

JP   06-054840    3/1994
JP   2003-153893  5/2003
(Continued)

OTHER PUBLICATIONS

Combined Chinese Office Action and Search Report issued Nov. 11, 2015 in Patent Application No. 201380004945.4 (with English translation of categories of cited documents).
(Continued)

*Primary Examiner* — Anastasia Midkiff
(74) *Attorney, Agent, or Firm* — Oblon, McClelland, Maier & Neustadt, L.L.P.

(57) ABSTRACT

An X-ray CT apparatus is provided which can easily decide on a reconstruction method based on imaging conditions. The X-ray CT apparatus comprises an irradiation unit irradiating a subject with X-rays, a detector configured to detect X-rays transmitted through the subject, and a rotator rotating irradiation unit and detector around the subject, and which generates an image by receiving biological signals of the subject to perform synchronous imaging. A memory stores a threshold value. Processing circuitry calculates, based on imaging conditions related to the synchronous imaging, a detection data amount in which detection data amount detected by the detector is represented by a number of rotations of the rotator, decides, based on the detection data
(Continued)

amount and the threshold value, on a reconstruction process for implementation on the detection data, and implements reconstruction processes based on the detection data to generate the image.

10 Claims, 8 Drawing Sheets

(52) U.S. Cl.
CPC .............. *A61B 6/5241* (2013.01); *A61B 6/541* (2013.01); *G06T 11/006* (2013.01); *G06T 2207/20004* (2013.01); *G06T 2211/412* (2013.01)

(58) Field of Classification Search
CPC ........ H05G 1/08; H05G 1/56; G03H 2210/00; G03H 2210/30; G03H 2210/33; G06T 11/00; G06T 11/003; G06T 11/005; G06T 11/006; G06T 2207/00; G06T 2207/10; G06T 2207/10072; G06T 2207/10081; G06T 2207/20; G06T 2207/20004; G06T 2211/00; G06T 2211/40; G06T 2211/412; G06T 2211/416
See application file for complete search history.

(56) References Cited

U.S. PATENT DOCUMENTS

| | | | | |
|---|---|---|---|---|
| 7,421,062 B2 * | 9/2008 | Okumura | ............... | A61B 6/032 378/116 |
| 7,532,750 B2 | 5/2009 | Sasaki et al. | | |
| 7,561,657 B2 * | 7/2009 | Nakanishi | ............. | A61B 6/032 378/15 |
| 8,559,687 B2 | 10/2013 | Chiang et al. | | |
| 2003/0099323 A1 * | 5/2003 | Nagata | ................... | A61B 6/032 378/4 |
| 2005/0175140 A1 | 8/2005 | Tsujii | | |
| 2005/0254721 A1 | 11/2005 | Hagiwara | | |
| 2009/0152471 A1 * | 6/2009 | Rousso | ................... | G01T 1/161 250/363.04 |
| 2010/0283779 A1 | 11/2010 | Chiang et al. | | |
| 2011/0103662 A1 | 5/2011 | Chiang et al. | | |
| 2011/0170757 A1 * | 7/2011 | Pan | ........................ | A61B 6/032 382/131 |
| 2012/0078083 A1 * | 3/2012 | McConnell | ............ | A61B 5/055 600/413 |
| 2013/0039457 A1 * | 2/2013 | Hiraoka | ................ | A61B 6/541 378/8 |
| 2013/0243299 A1 | 9/2013 | Goto et al. | | |

FOREIGN PATENT DOCUMENTS

| | | |
|---|---|---|
| JP | 2003-308543 | 10/2003 |
| JP | 2005-218601 | 8/2005 |
| JP | 2005-323926 | 11/2005 |
| JP | 2006-174949 | 7/2006 |
| JP | 2011-92692 | 5/2011 |
| WO | WO 2008/064367 A2 | 5/2008 |
| WO | 2012/077694 | 6/2012 |

OTHER PUBLICATIONS

International Search Report issued Nov. 5, 2013, in PCT/JP13/073192, filed Aug. 29, 2013.

* cited by examiner

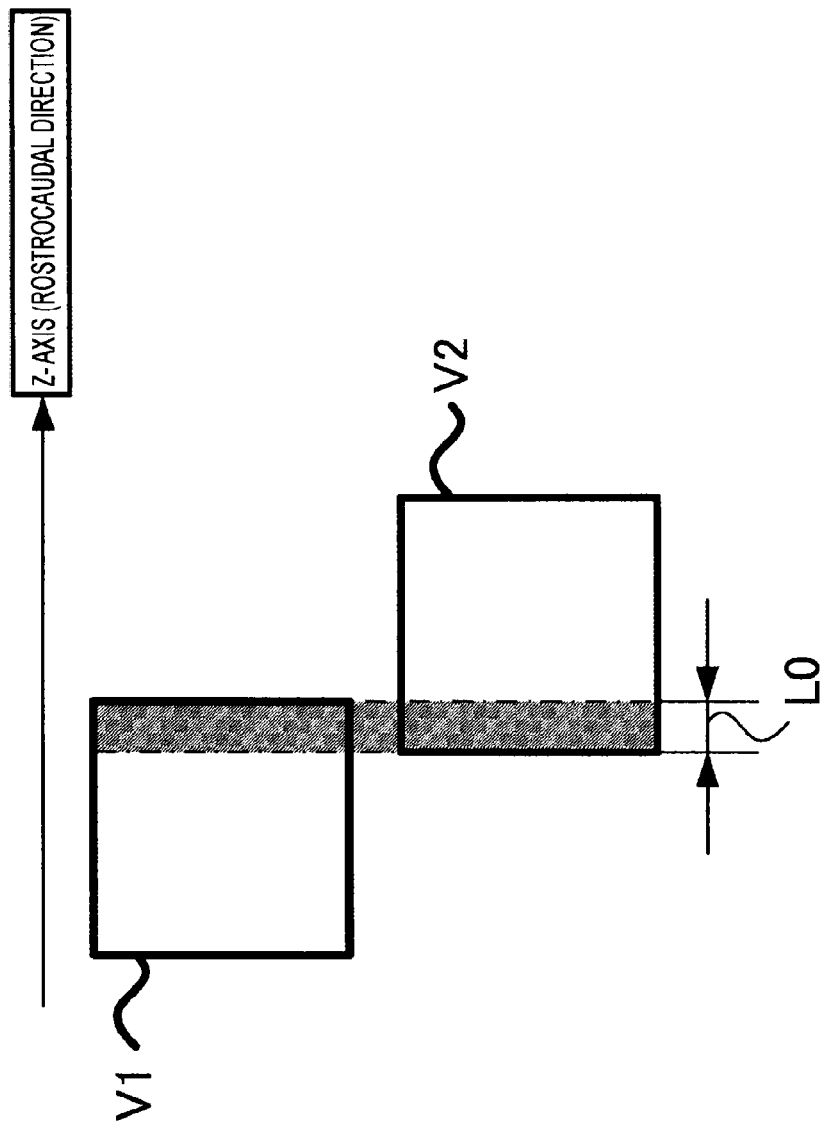

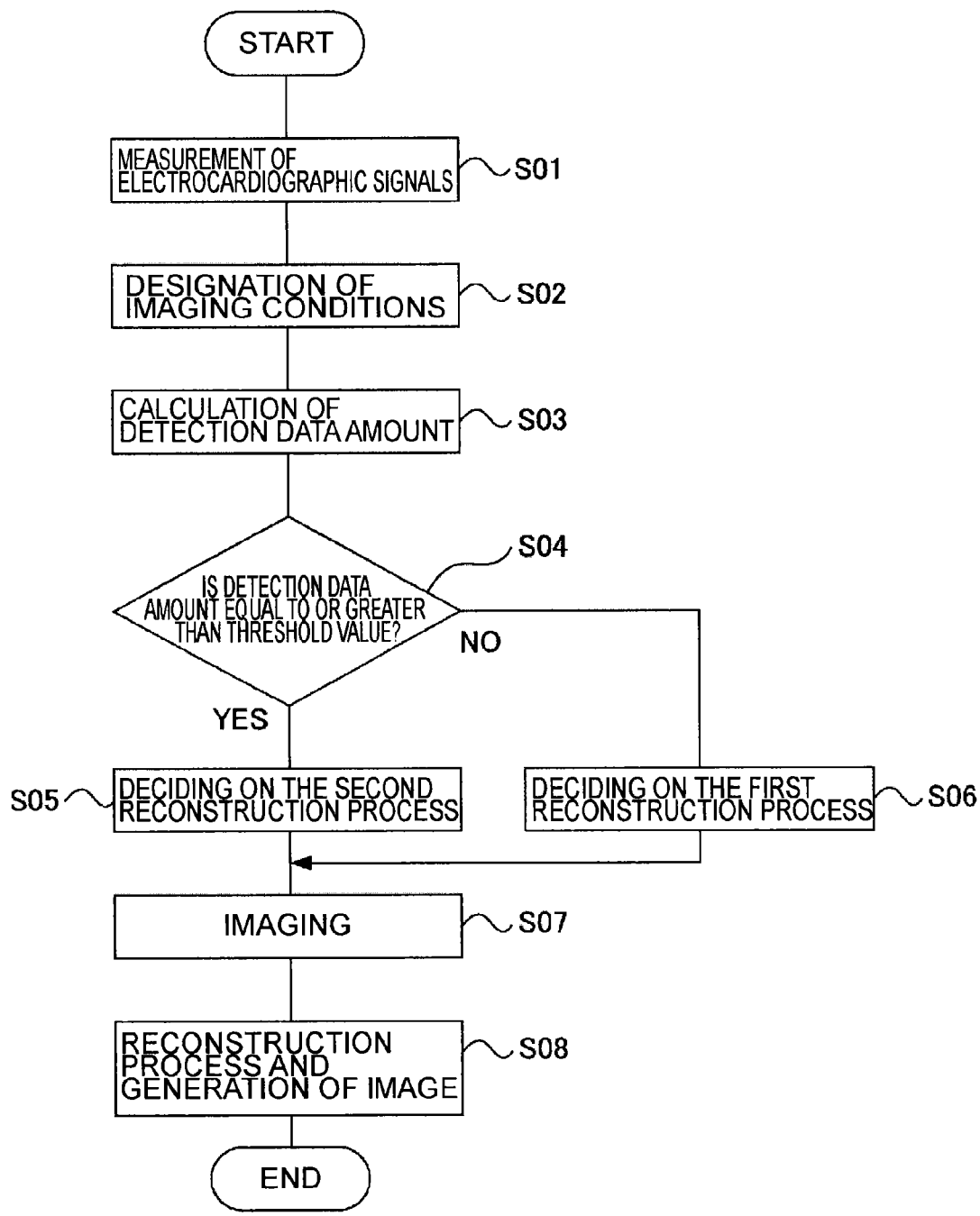

X-RAY CT APPARATUS

The embodiments of the present invention relate to an X-ray CT apparatus.

BACKGROUND OF THE INVENTION

An X-ray CT (Computed Tomography) apparatus is an apparatus which images the interior of a subject by scanning the subject with X-rays, acquiring detection data, and reconstructing the acquired detection data with a computer.

The X-ray CT apparatus comprises a rotator at which an X-ray tube and an X-ray detector are arranged opposite to each other on a circular frame, wherein the rotator is structured such that a subject is positioned inside the frame, irradiated with X-rays from the X-ray tube during rotation of the rotator, and scanned by detecting the X-rays transmitted through the subject with the X-ray detector.

Imaging methods using the X-ray CT apparatus include an imaging method known as step and shoot. In this method, after irradiating a part of a subject with X-rays to create an image, the subject with a couch is moved a prescribed distance in the rostrocaudal direction while stopping the irradiation of X-rays, another part of the subject is then irradiated with X-rays to create an image, and by repeating the operations of moving and imaging, and composing the images of each part of the subject, an image of a broader range of the subject is obtained. In general, the images of each part of the subject are imaged so as to include superposed regions (overlap regions) to be used for the composition.

Another imaging method using the X-ray CT apparatus is an imaging method known as synchronous (gated) imaging. In this method, biological signals of the subject are received and X-rays are irradiated at prescribed phases of these signals. Known examples of the synchronous imaging include ECG (electrocardiogram)-gated examination and respiratory-gated imaging.

The ECG-gated examination is a method in which electrocardiographic signals are received from an electrocardiograph as biological signals of the subject, and X-rays are irradiated at prescribed cardiac phases of these signals. With this method, in some cases, the remaining range in the prescribed cardiac phases may be set in advance to perform half imaging based on this remaining range.

The respiratory-gated imaging is a method in which respiratory signals are received from a respiratory measuring unit as biological signals of the subject, and X-rays are irradiated at prescribed respiratory phases of these signals. With this method, in some cases, the remaining range in the prescribed respiratory phases may be set in advance to perform the half imaging based on this remaining range.

Moreover, methods of reconstruction process used for a cone-beam X-ray CT apparatus which irradiates X-rays in a conical form include a method known as FDK (Feldkamp, Davis, Kress) reconstruction technique, as well as a method, in which the FDK reconstruction technique is expanded, known as image region expansion reconstruction technique. Images reconstructed using the FDK reconstruction technique are three-dimensional images in which the cross-sections parallel to the rostrocaudal direction of the subject (the sagittal cross-section and the coronal cross-section) form a hexagon. In comparison, images reconstructed using the image region expansion reconstruction technique are three-dimensional images in which the image region has been expanded so that the cross-sections parallel to the rostrocaudal direction of the subject form a rectangle.

In this way, the images created using the image region expansion reconstruction technique have the region broader than that of the images created using the FDK reconstruction technique. Consequently, with imaging using the image region expansion reconstruction technique, it is possible to obtain images over a broader range of the subject with fewer rounds of X-ray irradiation compared to imaging using the FDK reconstruction technique. Furthermore, due to the abovementioned variance in the shapes of the cross-sections parallel to the rostrocaudal direction of the subject, with imaging using the image region expansion reconstruction technique, it is possible to make the superposed regions of the images smaller compared to imaging using the FDK reconstruction technique. As a result, imaging using the image region expansion reconstruction technique allows for imaging with lower radiation exposure compared to imaging using the FDK reconstruction technique. However, it is known that the image region expansion reconstruction technique requires an amount of detection data that is at least equivalent to a full scan. In other words, the image region expansion reconstruction technique requires detection data that is the amount of detection data represented by a number of rotations of the rotator is 1 or more. Consequently, the feasibility of using image region expansion reconstruction technique depends on the amount of detection data. The amount of detection data is determined based on the imaging conditions (the rotational speed of the rotator, the abovementioned remaining range, and the like).

PRIOR ART DOCUMENT

Patent Document

[Patent Document 1] Japanese Published Unexamined Application No. 2011-92692

SUMMARY OF THE INVENTION

Problems to be Solved by the Invention

As described above, there are situations in which the image region expansion reconstruction technique can and cannot be used depending on the amount of detection data. Because there is a wide range of imaging conditions related to the amount of detection data, it is difficult for operators to assess those situations based on the imaging conditions, and decide on a method of reconstruction.

The present invention is intended to provide an X-ray CT apparatus which can easily decide on a reconstruction method based on imaging conditions.

Means for Solving the Problems

An X-ray CT apparatus of this embodiment comprises: an irradiation unit configured to irradiate a subject with X-rays, a detector configured to detect the X-rays transmitted through the subject, and a rotator configured to rotate the irradiation unit and the detector around the subject, and for generating an image by receiving biological signals of the subject to perform synchronous imaging, the X-ray CT apparatus, comprising: a memory; a calculator; a decision unit; and a processor. The memory is configured to store in advance a prescribed threshold value. The calculator is configured to, based on imaging conditions related to the synchronous imaging, calculate a detection data amount in which the detection data amount detected by the detector is represented by a number of rotations of the rotator. The decision unit is configured to, based on the detection data amount calculated by the calculator and the threshold value stored in the memory, decide on a reconstruction process for implementing on the detection data. The processor is configured to implement the reconstruction process decided on by the decision unit on the detection data, and generate the image.

BRIEF DESCRIPTION OF THE DRAWINGS

FIG. 3A It is a pattern diagram showing an outline of the X-ray CT apparatus of the embodiment.

FIG. 4 It is a flowchart showing an operation example of the X-ray CT apparatus of the embodiment.

MODES FOR CARRYING OUT THE INVENTION

X-ray CT apparatuses according to embodiments are described below with reference to the diagrams. Since "image" and "image data" have a one-to-one correlation, these two concepts may be viewed as the same in some cases.

<First Embodiment>

[Configuration]

Figure 1:
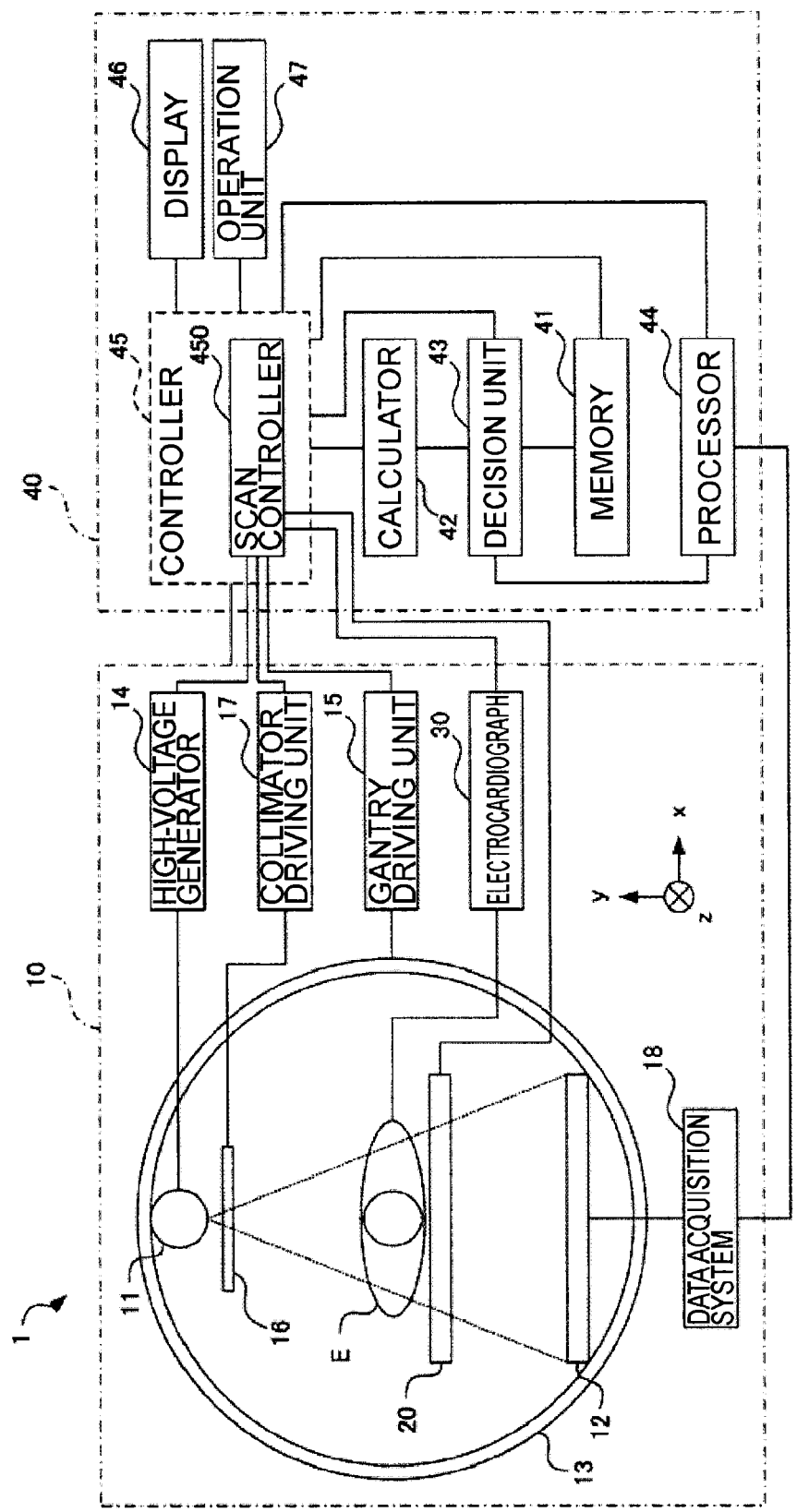
FIG. 1 It is a block diagram showing a configuration example of an X-ray CT apparatus of an embodiment.

FIG. 1 is a block diagram showing the configuration of an X-ray CT apparatus 1 of the present embodiment. The X-ray CT apparatus 1 receives biological signals including electrocardiographic signals from a subject E, and performs ECG-gated examination as synchronous imaging. The X-ray CT apparatus 1 comprises a gantry 10, a couch 20, an electrocardiograph 30, and a console 40.

(Gantry 10)

The gantry 10 irradiates the subject E with X-rays, and acquires detection data of the X-rays transmitted through the subject E. The gantry 10 comprises an irradiation unit 11, a detector 12, a rotator 13, a high-voltage generator 14, a gantry driving unit 15, a collimator 16, a collimator driving unit 17, and a data acquisition system 18.

The irradiation unit 11 irradiates the subject E with X-rays. The irradiation unit 11 is configured with, for example, an X-ray tube (not illustrated) that generates X-rays in a conical form.

The detector 12 detects the X-rays transmitted through the subject E. The detector 12 is configured with, for example, multiple X-ray detecting elements (not illustrated). The detector 12 detects X-ray strength distribution information (referred to as "detection data" in the present specification) indicating the strength distribution of the X-rays transmitted through the subject E, and outputs the detection data as electrical current signals.

For the detector 12, a two-dimensional X-ray detector (surface detector) in which the multiple detecting elements are arranged in, for example, in two perpendicular directions (slice direction and channel direction), respectively. By using such the two-dimensional X-ray detector, it is possible to obtain detection data (volume data) indicating a three-dimensional region with a width in the slice direction in a single scan (volume scan). The slice direction corresponds to the rostrocaudal direction of the subject E, and the channel direction corresponds to the rotational direction of the irradiation unit 11.

The rotator 13 rotates the irradiation unit 11 and the detector 12 around the subject E. The rotator 13 is a member that supports, for example, the irradiation unit 11 and the detector 12 at positions facing each other on opposing sides of the subject E. The rotator 13 comprises an opening that goes through in the slice direction. The couch 20 on which the subject E is mounted is inserted into the opening. The rotator 13 is rotated along a circular path with the subject E in the center by the gantry driving unit 15. The rotational speed of the rotator 13 is designated in advance via an operation unit 47 and a controller 45.

The high-voltage generator 14 applies a high voltage to the irradiation unit 11. The irradiation unit 11 generates X-rays based on the high voltage.

The collimator 16 forms a slit (opening), and changes the size and shape of the slit in order to adjust a fan angle FA (the spread angle in the channel direction) of the X-rays output from the irradiation unit 11 and the cone angle (the spread angle in the slice direction) of the X-rays. The collimator driving unit 17 drives the collimator 16 to change the size and shape of the slit.

The data acquisition system 18 acquires detection data from the detector 12 (each X-ray detecting element). Further, the data acquisition system 18 converts the acquired detection data (electrical current signals) into high-voltage signals, integrates and amplifies the high-voltage signals periodically, and converts the high-voltage signals into digital signals. The data acquisition system 18 then transmits the detection data converted into the digital signals to the console 40.

(Couch 20)

The couch 20 carries the subject E and moves the subject E in the rostrocaudal direction. The couch 20 may also move in upward and downward directions (y-axis direction).

(Electrocardiograph 30)

The electrocardiograph 30 measures the electrocardiographic signals of the subject E, and outputs the electrocardiographic signals to a scan controller 450. Further, based on the electrocardiographic signals measured in advance, the electrocardiograph 30 outputs the heart rate of the subject E to a calculator 42. The electrocardiograph 30 may be contained in the X-ray CT apparatus 1, or may be mounted on the exterior of the X-ray CT apparatus 1.

(Console 40)

The console 40 is used to input operations in the X-ray CT apparatus 1. Based on the detection data output from the gantry 10, the console 40 reconstructs CT image data (volume data) indicating the interior state of the subject E. The console 40 comprises a memory 41, the calculator 42, a decision unit 43, a processor 44, the controller 45, a display 46, and the operation unit 47.

The memory 41 stores a prescribed threshold value in advance. For example, the memory 41 stores a value indicating the number of rotations of the rotator 13 as the threshold value in advance. Here, a scan performed from when X-rays are generated by the irradiation unit 11 to when the X-ray generation is stopped shall be considered as a single scan. As described above, while a scan is being performed, the irradiation unit 11 and the detector 12 are rotated by the rotator 13. The prescribed threshold value is a threshold value indicating the amount of detection data required to use a prescribed reconstruction technique. For example, it is known that detection data corresponding to at least a full scan is required to use the abovementioned image region expansion reconstruction technique as the prescribed method of reconstruction. Consequently, the threshold value indicating the amount of detection data required to use the image region expansion reconstruction technique is 1. Moreover, the memory 41 stores in advance association information in which the threshold value is associated with a first reconstruction process that generates images based on the detection data as well as a second reconstruction process that generates an image of an expanded region compared to the image region generated by the first reconstruction process based on the detection data. For example, the memory 41 stores the FDK reconstruction technique as the first reconstruction process, and the image region expansion reconstruction technique as the second reconstruction process. The memory 41 also stores detection data, projection data, post-reconstruction image data, and the like.

Based on the imaging conditions related to the ECG-gated examination as the gating imaging, the calculator 42 calculates a detection data amount D, in which the amount of detection data detected by the detector 12 is indicated by the number of rotations of the rotator 13. Further, as the imaging conditions, the calculator 42 calculates the fan angle FA of the X-rays generated by the irradiation unit 11, the heart rate of the subject E, a remaining range PD related to a prescribed cardiac phase in the electrocardiographic signals, and the detection data amount D based on the rotational speed of the rotator 13.

Figure 2:
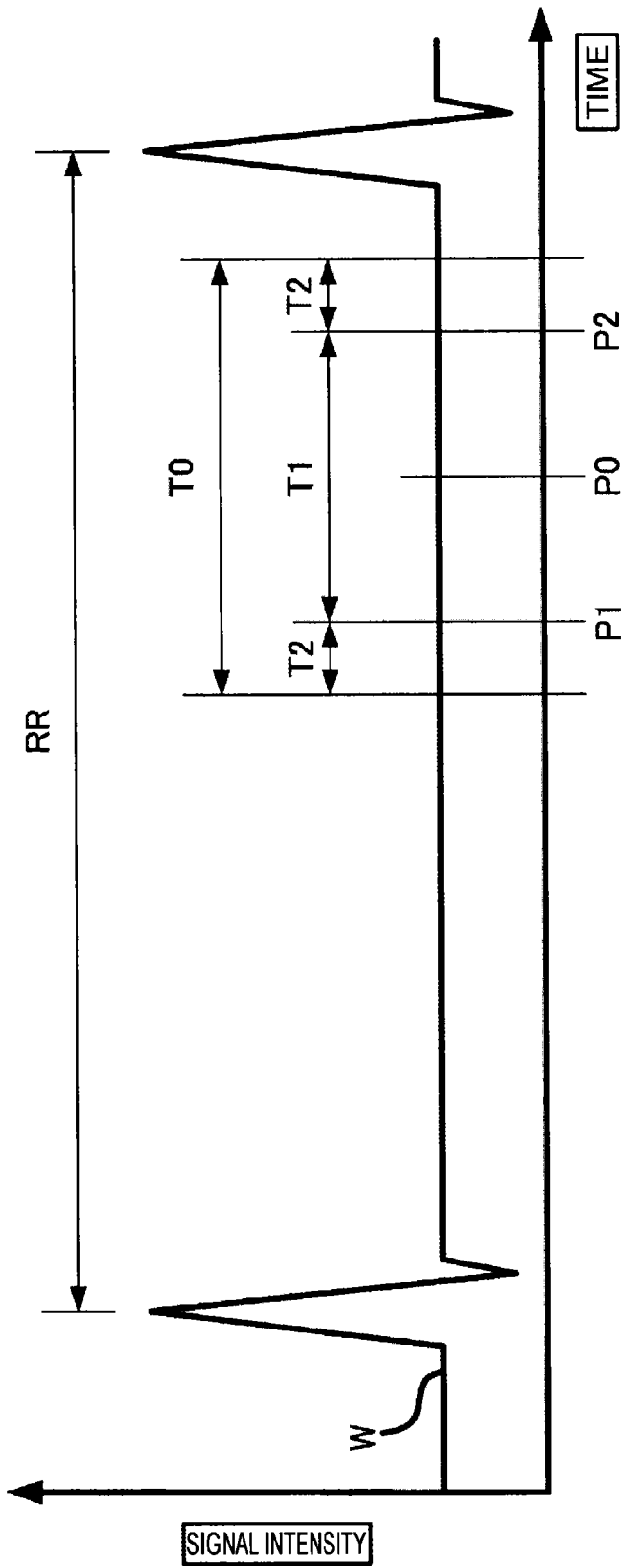
FIG. 2 It is a pattern diagram showing an outline of the X-ray CT apparatus of the embodiment.

The following is a description of the ECG-gated examination. FIG. 2 is a pattern diagram showing the relationship between an electrocardiographic waveform W based on the electrocardiographic signals of the subject E with the ECG-gated examination performed by the X-ray CT apparatus 1. The X-ray CT apparatus 1 irradiates X-rays at a prescribed time T0 with a prescribed cardiac phase P0 as the mean, and acquires detection data (a single scan). The prescribed cardiac phase P0 is designated in advanced via the operation unit 47 and the controller 45. The remaining range PD is designated in advance via the operation unit 47 and the controller 45, for example, in percentage, as a relative range to an interval RR between the R-peaks of the electrocardiographic waveform W. A first time T1 that has the cardiac phase P0 as the mean is determined by, for example, the following formula.

$$T1 = RR * \frac{PD}{100}$$ [Formula 1]

$$RR = \frac{60}{HR}$$

T1 : First time (seconds)
RR: R-peak interval (seconds)
PD: Remaining range (%)
HR: Heart rate (beats/minute)

The time T0 is a time obtained by adding a second time T2 before a starting point P1 of the first time T1 and after an endpoint P2 of the first time T1. For example, in a case of the half imaging, the second time T2 is obtained by using the following formula.

$$T2 = \frac{RS}{2} * \frac{1}{2}$$ [Formula 2]

RS: Rotational velocity (seconds/rotation)

The X-ray CT apparatus 1 irradiates X-rays and acquires detection data (a single scan) in the prescribed time T0 in which the first time T1 and the second time T2 are included with the prescribed cardiac phase P0 as the mean. The calculator 42 calculates the detection data amount D in this single scan. The detection data amount D is obtained by using, for example, the following formula.

$$D = \frac{\frac{T0}{RS} + \frac{FA}{360}} = \frac{T1 + 2*T2}{RS} + \frac{FA}{360} = \frac{\frac{60}{HR} * \frac{PD}{100}}{RS} + \frac{1}{2} + \frac{FA}{360}$$ [Formula 3]

$$T0 = T1 + 2*T2$$

D: Detection data amount (rotations)
FA: Fan angle (deg)

In this way, since the detection data amount D is obtained by dividing the amount of detection data detected by the detector 12 in a single scan by the amount of detection data detected by the detector 12 in a single rotation of the rotator 13, the detection data amount D is represented as the number of rotations of the rotator 13.

The decision unit 43 decides on the reconstruction process for implementing on the detection data based on the detection data amount D from the calculator 42 and the threshold value in the memory 41. At this time, the decision unit 43 receives association information from the memory 41, and decides on the reconstruction process associated with the threshold value as the reconstruction process for implementing on the detection data.

When the detection data amount D is equal to or greater than the threshold value, from among the first reconstruction process and the second reconstruction process in the association information, the decision unit 43 decides on the second reconstruction process as the reconstruction process for implementing on the detection data. For example, when the memory 41 stores the FDK reconstruction technique as the first reconstruction process and the image region expansion reconstruction technique as the second reconstruction process, the threshold value in the memory 41 is 1, and the detection data amount D is equal to or greater than 1, the decision unit 43 decides on the image region expansion reconstruction technique, which is the second reconstruction process, as the reconstruction process for implementing on the detection data. When the detection data amount D is below the threshold value, the decision unit 43 may decide on the FDK reconstruction method, which is the first reconstruction process, as the reconstruction process for implementing on the detection data.

Figure 3B:
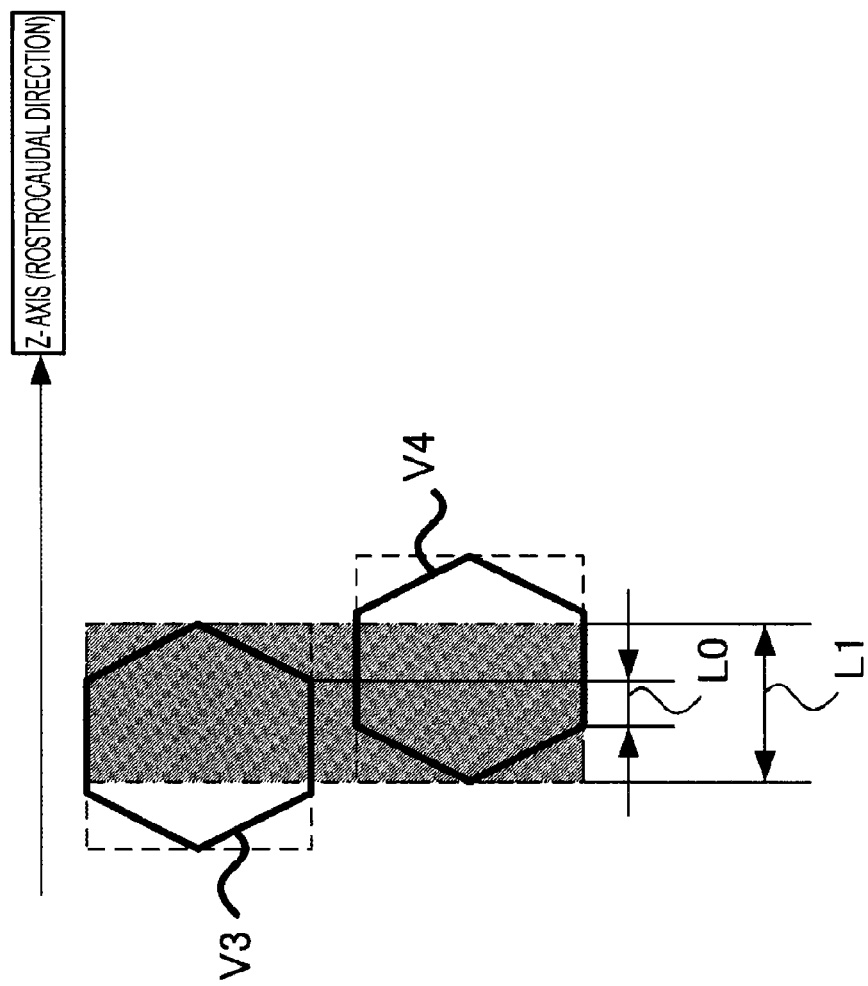
FIG. 3B It is a pattern diagram showing an outline of the X-ray CT apparatus of the embodiment.

In addition to deciding on the reconstruction process for implementing on the detection data, the decision unit 43 also decides on an overlap width of the images. The overlap width is stored in the memory 41. The overlap width is described now with reference to FIG. 3A and FIG. 3B. FIG. 3A and FIG. 3B are pattern diagrams showing regions where the detection data is reconstructed by the reconstruction process decided on by the decision unit 43. In FIG. 3A, an overlap width L0 between a region V1 and a region V2, which are reconstructed using the image region expansion reconstruction method, is a width indicating the region where the image related to the region V1 and the image related to the region V2 are composed. In FIG. 3B, the same applies to an overlap width L1 between a region V3 and a region V4, which are reconstructed using the FDK reconstruction method. The region V1, the region V2, the region V3 and the region V4 are regions where the reconstruction process is performed on the detection data detected through a single scan. The shaded regions are regions where X-rays are irradiated twice through the step-and-shoot imaging. As shown in FIG. 3A and FIG. 3B, imaging using the image region expansion reconstruction method is marked by the fact that the region (superposed region) where X-rays are irradiated twice is smaller than that created through imaging using the FDK reconstruction method. Consequently, when the detection data can be obtained at an amount allowing for the use of the image region expansion reconstruction method, the decision unit 43 is able to reduce radiation exposure by deciding on the image region expansion reconstruction method as the reconstruction process for implementing on the detection data.

The processor 44 implements the reconstruction process decided on by the decision unit 43 on the detection data to generate an image. The processor 44 performs preliminary processes, including logarithmic conversion processing, offset correction, sensitivity correction, beam hardening correction, and the like, on the detection data from the data acquisition system 18

Based on the detection data that has undergone the preliminary processing, the processor 44 generates image data (volume data). In the processor 44, the reconstruction process decided on by the decision unit 43 is used as the reconstruction process for image data generation. Through the volume scan using the abovementioned multi-row two-dimensional X-ray detector, volume data over a broad range is reconstructed.

The processor 44 is able to execute, for example, MPR (Multi Planer Reconstruction) processing or volume rendering. The MPR processing is an image process in which a cross-section is arbitrarily set in generated volume data and a rendering process is implemented to generate MPR image data representing the cross-section. The volume rendering is an image process in which volume data is sampled along an arbitrary line of sight (ray) and the values thereof (CT value) are added to generate pseudo three-dimensional image data representing a three-dimensional region of the subject E.

The controller 45 controls each part of the apparatus. The controller 45 is configured with, for example, a processing apparatus and a storing device. Examples of the processing apparatus include a CPU (Central Processing Unit), a GPU (Graphic Processing Unit), or an ASIC (Application Specific Integrated Circuit). The storing device is configured with, for example, a ROM (Read Only Memory), a RAM (Random Access Memory), or a HDD (Hard Disc Drive). Computer programs for executing the functions of each part of the X-ray CT apparatus 1 are stored in the storing device. The processing apparatus realizes the above functions by executing these computer programs. The controller 45 comprises the scan controller 450.

The scan controller 450 comprehensively controls operations related to scanning using X-rays. This comprehensive control includes control of the high-voltage generator 14, control of the gantry driving unit 15, control of the collimator driving unit 17, and control of the couch 20. Control of the high-voltage generator 14 refers to control of the high-voltage generator 14 so that a prescribed high-voltage is applied to the irradiation unit 11 at a prescribed timing. Control of the gantry driving unit 15 refers to control of the gantry driving unit 15 to drive and rotate the rotator 13 at a prescribed timing and a prescribed velocity. The prescribed timing refers to the timing of irradiation and a stoppage of the irradiation of X-rays during the ECG-gated examination.

The scan controller 450 receives the X-ray fan angle FA designated in advance via the operation unit 47, the remaining range PD and a rotational speed RS of the rotator 13, and a heart rate HR of the subject E from the electrocardiograph 30, and decides on the timing. Control of the collimator controller 45 refers to control of the collimator driving unit 17 so that the collimator 16 forms a slit with a prescribed size and shape. Control of the couch 20 refers to control of the couch 20 so that the couch 20 is arranged at a prescribed position at a prescribed timing. As a result of this control, the couch 20 is moved to and stopped at a position (prescribed position) corresponding to an overlap amount determined by the decision unit 43. Under a volume scan, the scan is executed while the position of the couch 20 is fixed.

The display 46 is configured by a display device, such as an LCD (Liquid Crystal Display), or the like. The display 46 may be contained in the X-ray CT apparatus 1, or may be mounted on the exterior of the X-ray CT apparatus 1. The operation unit 47 is configured by, for example, a keyboard, a mouse, a trackball, a joystick, or the like. Further, the operation unit 47 may include a GUI (Graphical User Interface) displayed on the display 46. The operation unit 47 may be contained in the X-ray CT apparatus 1, or may be mounted on the exterior of the X-ray CT apparatus 1.

[Operation]

FIG. 4 is a flowchart showing an operation of the X-ray CT apparatus 1 of the present embodiment.

(S01)

The electrocardiograph 30 measures electrocardiographic signals of the subject E, and outputs the heart rate HR based on those electrocardiographic signals to the scan controller 450.

(S02)

The scan controller 450 receives a designation of imaging conditions related to the ECG-gated examination via the operation unit 47. Here, the imaging conditions may include the prescribed cardiac phase P0, the X-ray fan angle FA, the remaining range PD, and the rotational speed RS of the rotator 13.

(S03)

The controller 45 controls the calculator 42, and based on the imaging conditions related to the ECG-gated examination, calculates the detection data amount D, in which the amount of the detection data detected by the detector 12 is represented by the number of rotations of the rotator 13.

(S04, S05)

When the detection data amount D is equal to or greater than the threshold value stored in advance in the memory 41, the controller 45 controls the decision unit 43, and decides on the second reconstruction process as the reconstruction process for implementing on the detection data from among the first reconstruction process and the second reconstruction process in the association information in the memory 41.

(S04, S06)

When the detection data amount D is less than the threshold value stored in advance in the memory 41, the controller 45 controls the decision unit 43, and decides on the first reconstruction process as the reconstruction process for implementing on the detection data, from among the first reconstruction process and the second reconstruction process in the association information in the memory 41.

(S07)

Based on the electrocardiographic signals of the subject E from the electrocardiograph 30 and the designated imaging conditions, the scan controller 450 controls the high-voltage generator 14, the gantry driving unit 15, the collimator driving unit 17, and the couch 20, and performs the ECG gated examination. As a result, the irradiation unit 11 irradiates the subject E with X-rays, the detector 12 detects the X-rays transmitted through the subject E, and the rotator 13 rotates the irradiation unit 11 and the detector 12 around the subject E.

(S08)

The controller 45 controls the processor 44, and causes the implementation of the reconstruction process of the processing method decided on by the decision unit 43 on the detection data to generate an image. Through the processes described above, the operation shown in FIG. 4 is completed.

[Operation and Effect]

The operation and effects of the X-ray CT apparatus 1 of the present embodiment are described below.

The X-ray CT apparatus 1 having the irradiation unit 11 which irradiates the subject E with X-rays, the detector 12 which detects the X-rays that have been transmitted through the subject E, and the rotator 13 which rotates the irradiation unit 11 and the detector 12 around the subject E, for generating images by receiving biological signals including electrocardiographic signals from the subject E and performing the ECG gated examination as the synchronous imaging, comprises the memory 41, the calculator 42, the decision unit 43, and the processor 44. The memory 44 stores in advance a threshold value. Based on the imaging conditions related to the ECG gated examination as the synchronous imaging, the calculator 42 calculates the detection data amount D, in which the amount of detection data detected by the detector 12 is represented by the number of rotations of the rotator 13. The decision unit 43 decides on the reconstruction process for implementing on the detection data based on the detection data amount D from the calculator 42 and the threshold value from the memory 41. The processor 44 implements the reconstruction process decided on by the decision unit 43 on the detection data to generate an image. In this way, the X-ray CT apparatus 1 easily decides on a reconstruction process corresponding to the detection data amount D based only on the size relationship with the threshold value, and generates an image using the reconstruction process. As a result, an X-ray CT apparatus that enables the easy determination of a reconstruction method based on imaging conditions can be provided.

<Second Embodiment>

[Configuration]

Figure 5:
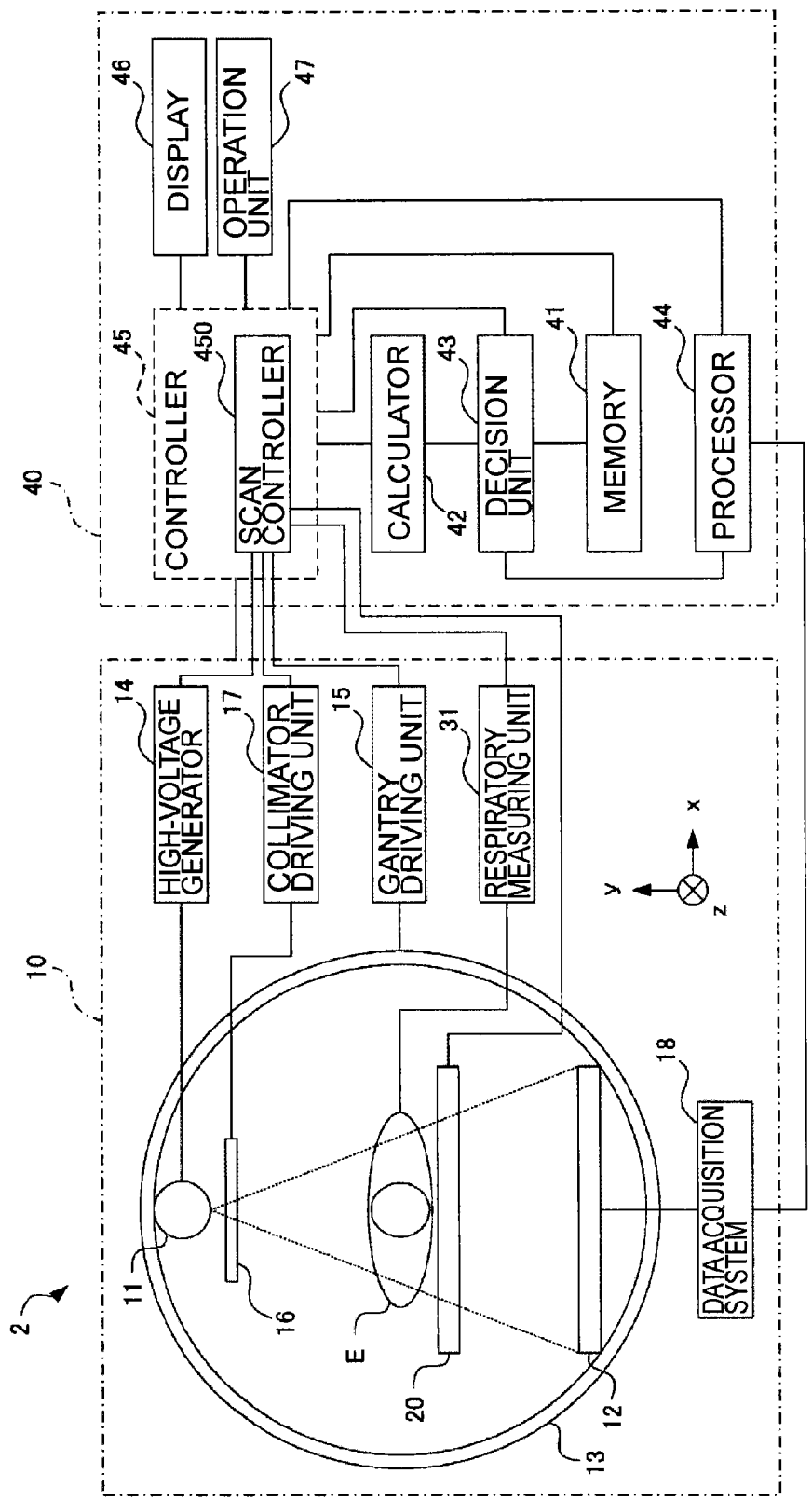
FIG. 5 It is a block diagram showing a configuration example of an X-ray CT apparatus of an embodiment.

FIG. 5 is a block diagram showing the configuration of an X-ray CT apparatus 2 of the present embodiment. The X-ray CT apparatus 2 receives biological signals including respiratory signals from the subject E, and implements the respiratory gated imaging as the synchronous imaging. Hereinafter, it describes configurations different from that of the first embodiment. Aspects similar to the first embodiment may be omitted in some instances. The X-ray CT apparatus 2 comprises the gantry 10, the couch 20, a respiratory measuring unit 31, and the console 40.

The respiratory measuring unit 31 measures respiratory signals of the subject E, and outputs the respiratory signals to the scan controller 450. For example, the respiratory measuring unit 31 measures temporal changes in the position of the chest surface of the subject E as the respiratory signals using an optical sensor (not illustrated). Further, the respiratory measuring unit 31 may measure temporal changes in the chest circumference of the subject E as the respiratory signals using a chest sensor (not illustrated) wrapped around the chest area of the subject E. The respiratory measuring unit 31 also outputs the breathing rate of the subject E to the calculator 42, based on the respiratory signals measured in advance. The respiratory measuring unit 31 may be contained in the X-ray CT apparatus 2, or may be mounted on the exterior of the X-ray CT apparatus 2.

Based on the imaging conditions related to the respiratory gated imaging as the gating imaging, the calculator 42 calculates a detection data amount Db, in which the amount of detection data detected by the detector 12 is represented by the number of rotations of the rotator 13. The calculator 42 also calculates the detection data amount Db, based on the following imaging conditions: the fan angle FA of the X-rays from the irradiation unit 11, the breathing rate of the subject E, the remaining range PD related to a prescribed respiratory phase in the respiratory signals, and the rotational speed of the rotator 13.

Figure 6:
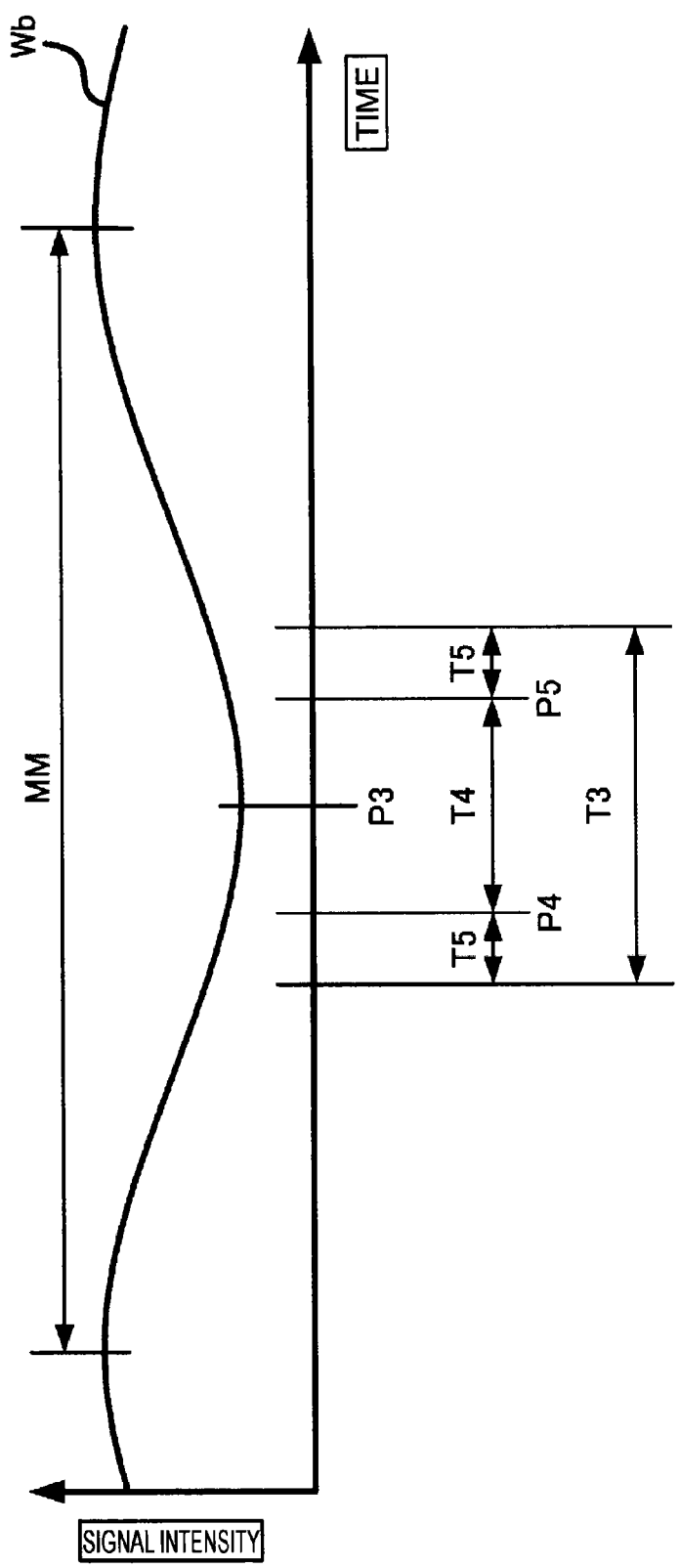
FIG. 6 It is a pattern diagram showing an outline of the X-ray CT apparatus of the embodiment.

The following is a description of the respiratory gated imaging. FIG. 6 is a pattern diagram showing the relationship between a respiratory waveform Wb based on the respiratory signals of the subject E and the respiratory gated imaging performed by the X-ray CT apparatus 2. The X-ray CT apparatus 2 irradiates X-rays and acquires detection data (a single scan) during a prescribed time T3 with a prescribed respiratory phase P3 as the mean. The prescribed respiratory phase P3 is designated in advance via the operation unit 47 and the controller 45. The remaining range PD is designated in advance via the operation unit 47 and the controller 45, for example, in percentage, as a relative range to an interval MM between the peaks of the respiratory waveform Wb. A third time T4 which has the respiratory phase P3 as its mean is obtained by, for example, the following formula.

$$T4 = MM * \frac{PD}{100} \qquad \text{[Formula 4]}$$

$$MM = \frac{60}{BR}$$

T4: Third time (seconds)
MM: Peak interval (seconds)
PD: Remaining range (%)
BR: Respiratory rate (breaths/minute)

The time T3 is a time obtained by adding a fourth time T5 before a starting point P4 of the third time T4 and after an endpoint P5 of the third time T4. In a case of the half imaging, for example, the fourth time T5 is obtained through the following formula.

$$T5 = \frac{RS}{2} * \frac{1}{2} \qquad \text{[Formula 5]}$$

RS: Rotational velocity (seconds/rotation)

The X-ray CT apparatus 2 irradiates X-rays and acquires detection data (a single scan) during the prescribed time T3 in which the third time T4 and the fourth time T5 are included with the prescribed respiratory phase P3 as the mean. The calculator 42 calculates the detection data amount Db in this single scan. The detection data amount Db is obtained by, for example, the following formula.

$$Db = \qquad \text{[Formula 6]}$$

$$\frac{T3}{RS} + \frac{FA}{360} = \frac{T4 + 2*T5}{RS} + \frac{FA}{360} = \frac{\frac{60}{BR} * \frac{PD}{100}}{RS} + \frac{1}{2} + \frac{FA}{360}$$

$$T3 = T4 + 2*T5$$

Db: Detection data amount (rotations)
FA: Fan angle (deg)

In this way, since the detection data amount Db is obtained by dividing the amount of detection data detected by the detector 12 in a single scan by the amount of detection data detected by the detector 12 in a single rotation of the rotator 13, the detection data amount Db is represented as the number of rotations of the rotator 13.

The decision unit 43 decides on the reconstruction process for implementing on the detection data based on the detection data amount Db from the calculator 42 and the threshold value in the memory 41. The scan controller 450 also comprehensively controls operations related to scanning using X-rays. This comprehensive control includes control of the gantry driving unit 15. Control of the gantry driving unit 15 refers to control of the gantry driving unit 15 to drive and rotate the rotator 13 at a prescribed timing and a prescribed velocity. The prescribed timing refers to the timing of irradiation and a stoppage of the irradiation of X-rays during the respiratory gated imaging. The scan controller 450 receives the X-ray fan angle FA designated in advance via the operation unit 47, the remaining range PD and the rotational speed RS of the rotator 13, and a breathing rate BR of the subject E from the respiratory measuring unit 31 to decide on the timing.

[Operation]

Figure 7:
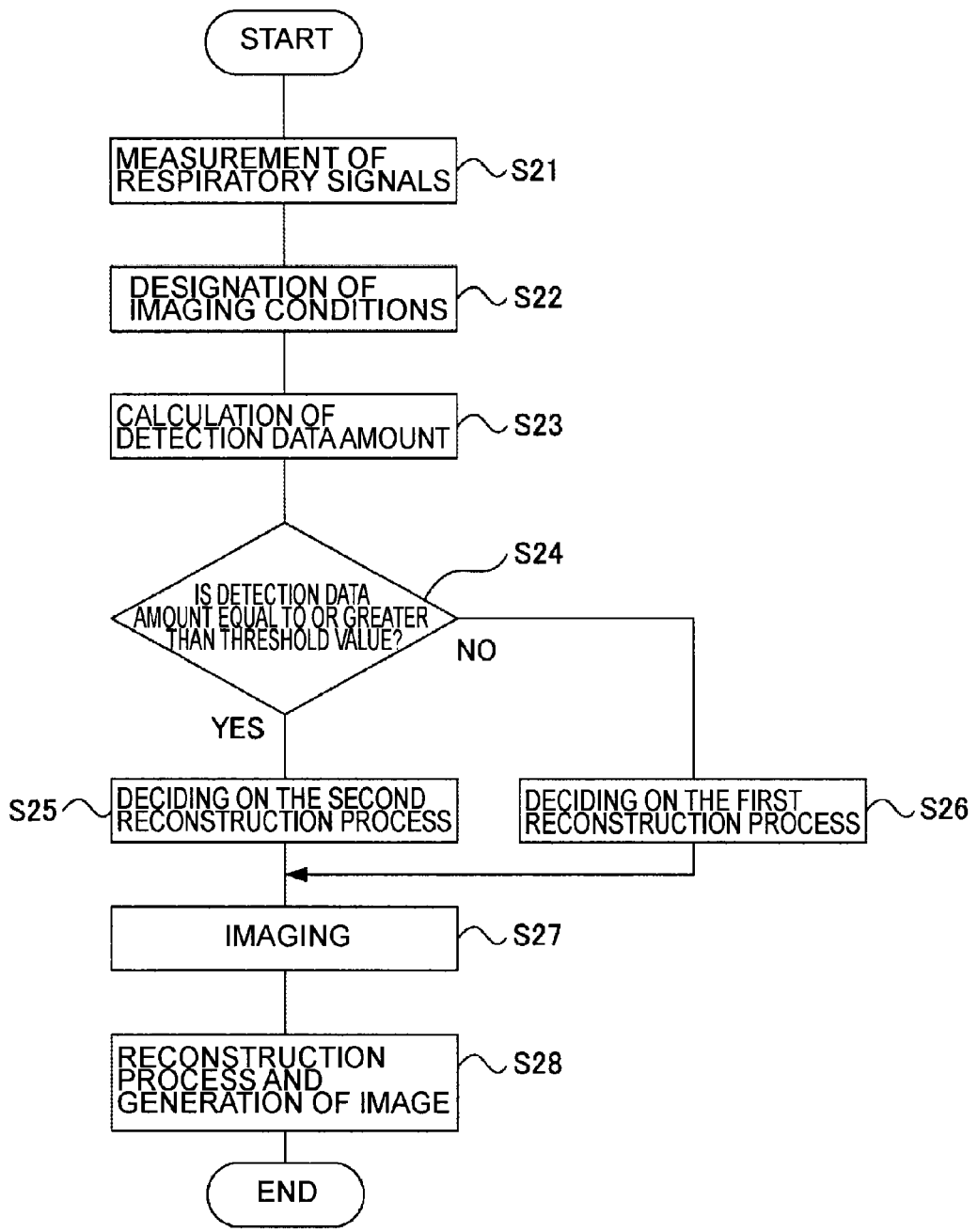
FIG. 7 It is a flowchart showing an operation example of the X-ray CT apparatus of the embodiment.

FIG. 7 is a flowchart showing an operation of the X-ray CT apparatus according to the present embodiment.

(S21)

The respiratory measuring unit 31 measures the respiratory signals of the subject E, and outputs the breathing rate BR based on the respiratory signals to the scan controller 450.

(S22)

The scan controller 450 receives a designation of imaging conditions related to the respiratory gated imaging via the operation unit 47. Here, the imaging conditions may include the prescribed respiratory phase P3, the X-ray fan angle FA, the remaining range PD, and the rotational speed RS of the rotator 13.

(S23)

The controller 45 controls the calculator 42, and, based on the imaging conditions related to the respiratory gated imaging, calculates the detection data amount Db, in which the amount of detection data detected by the detector 12 is represented by the number of rotations of the rotator 13.

(S24, S25)

When the detection data amount Db is equal to or greater than the threshold value stored in advance in the memory 41, the controller 45 controls the decision unit 43 to decide on the second reconstruction process as the reconstruction process for implementing on the detection data from among the first reconstruction process and the second reconstruction process in the association information in the memory 41.

(S24, S26)

When the detection data amount Db is less than the threshold value stored in advance in the memory 41, the controller 45 controls the decision unit 43 to decide on the first reconstruction process as the reconstruction process for implementing on the detection data from among the first reconstruction process and the second reconstruction process in the association information in the memory 41.

(S27)

Based on the respiratory signals of the subject E from the respiratory measuring unit 31 and the designated imaging conditions, the scan controller 450 controls the high-voltage generator 14, the gantry driving unit 15, the collimator driving unit 17, and the couch 20, performs the respiratory gated imaging. As a result, the irradiation unit 11 irradiates the subject E with X-rays, the detector 12 detects the X-rays transmitted through the subject E, and the rotator 13 rotates the irradiation unit 11 and the detector 12 around the subject E.

(S28)

The controller 45 controls the processor 44, and causes the implementation of the reconstruction process of the processing method decided on by the decision unit 43 on the detection data to generate an image. Through the processes described above, the operation shown in FIG. 7 is complete.

[Operation and Effect]

The operation and effects of the X-ray CT apparatus 2 of the present embodiment are described below.

The X-ray CT apparatus 2 having the irradiation unit 11 which irradiates the subject E with X-rays, the detector 12 which detects X-rays that have been transmitted through the subject E, and the rotator 13 which rotates the irradiation unit 11 and the detector 12 around the subject E, for receiving biological signals including the respiratory signals from the subject E, and performing the respiratory gated imaging as the synchronous imaging to generate images, comprises the memory 41, the calculator 42, the decision unit 43, and the processor 44. The memory 41 stores a prescribed threshold value in advance. Based on the imaging conditions related to the respiratory gated imaging, the calculator 42 calculates the detection data amount Db, in which the amount of detection data detected by the detector 12 is represented by the number of rotations of the rotator 13. The decision unit 43 decides on the reconstruction process for implementing on the detection data, based on the detection data amount Db from the calculator 42 and the threshold value in the memory 41. The processor 44 implements the reconstruction process decided on by the decision unit 43, and generates an image. In this way, the X-ray CT apparatus 2 easily decides on a reconstruction process corresponding to the detection data amount Db based only on the size relationship with the threshold value, and generates an image using the reconstruction process. As a result, an X-ray CT apparatus that enables the easy determination of a reconstruction method based on imaging conditions can be provided.

<Common Effects of the Embodiments>

With an X-ray CT apparatus according to at least one embodiment described above, it is possible to easily decide on a reconstruction method corresponding to imaging conditions by deciding on the reconstruction process for implementing on detection data based on a detection data amount calculated based on imaging conditions and a threshold value stored in advance.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

EXPLANATION OF SYMBOLS 1, 2 X-ray CT apparatus
10 Gantry
11 Irradiation unit
12 Detector
13 Rotator
14 High-voltage generator
15 Gantry driving unit
16 Collimator
17 Collimator driving unit
18 Data acquisition system
20 Couch
30 Electrocardiograph
31 Respiratory measuring unit
40 Console
41 Memory
42 Calculator
43 Decision unit
44 Processor
45 Controller
46 Display
47 Operation unit
450 Scan controller

The invention claimed is:

1. An X-ray CT apparatus having an irradiation unit configured to irradiate a subject with X-rays, a detector configured to detect the X-rays transmitted through the subject, and a rotator configured to rotate the irradiation unit and the detector around the subject, wherein the X-ray CT apparatus generates an image by receiving biological signals of the subject to perform synchronous imaging, the X-ray CT apparatus comprising:
a memory configured to store a prescribed threshold value; and
processing circuitry configured to
calculate, based on imaging conditions related to the synchronous imaging, a detection data amount in which the detection data amount detected by the detector is represented by a number of rotations of the rotator;
decide, based on the detection data amount and the threshold value stored in the memory, on a reconstruction process for implementing on the detection data;
implement the reconstruction process on the detection data; and
generate the image.

2. The X-ray CT apparatus according to claim 1, wherein the memory is configured to store a value representing the number of rotations as the threshold value.

3. The X-ray CT apparatus according to claim 1, wherein the memory is configured to store association information, in which the threshold value is associated with a first reconstruction process that generates images based on the detection data, and with a second reconstruction process that generates an image of an expanded region of an image generated by the first reconstruction process based on the detection data, and
the processing circuitry is configured to decide on the second reconstruction process as the reconstruction process for implementing on the detection data from among the first reconstruction process and the second reconstruction process in the association information, when the detection data amount is equal to or greater than the threshold value.

4. The X-ray CT apparatus according to claim 1, wherein the biological signals include electrocardiographic signals; and
the processing circuitry is configured to calculate the detection data amount based on the following imaging conditions: a fan angle of X-rays from the irradiation unit, the heart rate of the subject, a range in a prescribed cardiac phase in the electrocardiographic signals, and a rotational speed of the rotator.

5. The X-ray CT apparatus according to claim 1, wherein the biological signals include respiratory signals, and
the processing circuitry is configured to calculate the detection data amount based on the following imaging conditions: a fan angle of X-rays from the irradiation unit, the breathing rate of the subject, a range in a prescribed respiratory phase in the respiratory signals, and a rotational speed of the rotator.

6. The X-ray CT apparatus according to claim 2, wherein the memory is configured to store association information, in which the threshold value is associated with a first reconstruction process that generates images based on the detection data, and with a second reconstruction process that generates an image of an expanded region of an image generated by the first reconstruction process based on the detection data, and
the processing circuitry is configured to decide on the second reconstruction process as the reconstruction process for implementing on the detection data from among the first reconstruction process and the second reconstruction process in the association information, when the detection data amount is equal to or greater than the threshold value.

7. The X-ray CT apparatus according to claim 2, wherein the biological signals include electrocardiographic signals, and
the processing circuitry is configured to calculate the detection data amount based on the following imaging conditions: a fan angle of X-rays from the irradiation unit, the heart rate of the subject, a range in a prescribed cardiac phase in the electrocardiographic signals, and a rotational speed of the rotator.

8. The X-ray CT apparatus according to claim 2, wherein the biological signals include respiratory signals, and
the processing circuitry is configured to calculate the detection data amount based on the following imaging conditions: a fan angle of X-rays from the irradiation unit, the breathing rate of the subject, a range in a prescribed respiratory phase in the respiratory signals, and a rotational speed of the rotator.

9. The X-ray CT apparatus according to claim 3, wherein the biological signals include electrocardiographic signals, and
the processing circuitry is configured to calculate the detection data amount based on the following imaging conditions: a fan angle of X-rays from the irradiation unit, the heart rate of the subject, a range in a prescribed cardiac phase in the electrocardiographic signals, and a rotational speed of the rotator.

10. The X-ray CT apparatus according to claim 3, wherein the biological signals include respiratory signals, and
the processing circuitry is configured to calculate the detection data amount based on the following imaging conditions: a fan angle of X-rays from the irradiation unit, the breathing rate of the subject, a range in a prescribed respiratory phase in the respiratory signals, and a rotational speed of the rotator.

* * * * *